United States Patent [19]

Bohlmann et al.

[11] Patent Number: 5,145,847
[45] Date of Patent: Sep. 8, 1992

[54] 14,17α-ETHENO- AND -ETHANOESTRATRIENES, PROCESSES FOR THE PREPARATION OF THESE COMPOUNDS, AS WELL AS THEIR USE FOR THE PRODUCTION OF MEDICINAL AGENTS

[75] Inventors: Rolf Bohlmann; Hermann Künzer; Rudolf Wiechert; David Henderson; Martin Schneider; Yukishige Nishino, all of Berlin, Fed. Rep. of Germany

[73] Assignee: Schering Aktiengesellschaft, Berlin & Bergkamen, Fed. Rep. of Germany

[21] Appl. No.: 558,340

[22] Filed: Jul. 27, 1990

[30] Foreign Application Priority Data

Jul. 28, 1989 [DE] Fed. Rep. of Germany ....... 3925507

[51] Int. Cl.[5] .............................................. A61K 31/56
[52] U.S. Cl. .................................... 514/182; 552/510
[58] Field of Search ................ 552/511, 510; 514/182

[56] References Cited

U.S. PATENT DOCUMENTS 4,659,516 4/1987 Bowler et al. ..................... 514/144
4,789,671 12/1988 Bull et al. ............................ 514/182

FOREIGN PATENT DOCUMENTS 138504 4/1985 European Pat. Off. .

OTHER PUBLICATIONS

Fessenden and Fessenden "Organic Chemistry, 2nd ed." (1982) pp. 82, 287–289, 409–411, 525, 616, 639, 718, 865.

(List continued on next page.)

Primary Examiner—Mukund J. Shah
Assistant Examiner—Matthew V. Grambling
Attorney, Agent, or Firm—Millen, White & Zelano

[57] ABSTRACT

Disclosed are novel 14,17α-etheno- and -ethanoestratrienes according to general Formula I

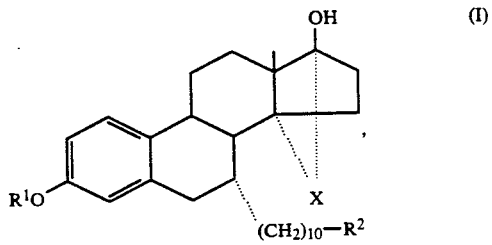

wherein
X is a $-CH_2-CH_2$ or

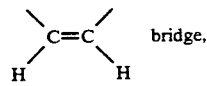

bridge, $R^1$ is a hydrogen atom, a $C_1$- to $C_{15}$-acyl, benzoyl, $C_1$- to $C_{15}$-alkyl, $C_3$- to $C_9$-cycloalkyl or alkylcycloalkyl group, and
$R^2$ is the grouping

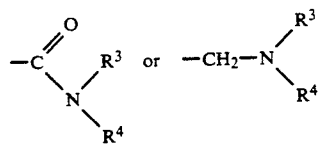

wherein $R^3$ and $R^4$ independently of each other mean a hydrogen atom or a straight-chain or branched, optionally partially or completely fluorinated $C_1$-$C_8$-alkyl group, a process for their preparation, pharmaceutical preparations containing these compounds, as well as their use for the production of medicinal agents.

The novel compounds exhibit strong antiestrogenic efficacy.

11 Claims, 3 Drawing Sheets

OTHER PUBLICATIONS

Gottardis et al., "Effect of Steroidal and Nonsteroidal Antiestrogens on the Growth of a Tamoxifen-stimulated Human Endometrical Carcinoma (EnCa1O1) in Athymic Mice," Cancer Research 50, 3189 3192, Jun. 1, 1990.

Wakeling, "Therapeutic Potential of Pure Antioestrogens in the Treatment of Breast Cancer," J. Steroid Biochem. Molec. Biol., vol. 37, No. 6, pp. 771-772 (1990).

Wakeling et al., "Antioestrogenic and Antitumor Activities of a Series of Non-Steroidal Antioestrogens," J. Endocr. 99, pp. 455-456 (1983).

Habenicht et al., "Induction of Estrogen-Related Hyperplastic Changes in the Prostate of the Cynomolgus Monkey (*Macaca fascicularis*) by Androstenedione and its Antagonization by the Aromatase Inhibitor 1-Methyl-Androsta-1,4-Diene-3,17-Dione," The Prostate 11:313-326 (1987).

14,17α-ETHENO- AND -ETHANOESTRATRIENES, PROCESSES FOR THE PREPARATION OF THESE COMPOUNDS, AS WELL AS THEIR USE FOR THE PRODUCTION OF MEDICINAL AGENTS

SUMMARY OF THE INVENTION

The present invention relates to 14,17α-etheno- and -ethanoestratrienes of general Formula I wherein
X is a —CH$_2$—CH$_2$ or bridge, R$_1$ is a hydrogen atom, a C$_1$— to C$_{15}$-acyl, benzoyl, C$_1$- to C$_{15}$-alkyl, C$_3$- to C$_9$-cycloalkyl or alkylcycloalkyl group, and
R$^2$ is the grouping wherein R$^3$ and R$^4$ independently of each other mean a hydrogen atom or a straight-chain or branched, optionally partially or completely fluorinated C$_1$-C$_8$-alkyl group,
to a process for their preparation, to pharmaceutical preparations containing these compounds, as well as to their use for the production of medicinal agents. Preferred embodiments of the present invention can be seen from the features of the dependent claims.

In the compounds of this invention, suitable C$_{1-15}$-acyl groups are preferably C$_{1-15}$-alkanoyl groups such as formyl, acetyl, i-propanoyl, n-propanoyl, isomers of butanoyl, pentanoyl, heptanoyl, decanoyl, dodecanoyl, etc.; suitable alkyl groups (1-15 or 1-8 carbon atoms in accordance with the foregoing) include methyl, ethyl, i-propyl, n-propyl, i-, n-, sec-, t-butyl, and isomers of pentyl, hexyl, octyl, decyl, undecyl, dodecyl, etc. For R$^3$ and R$^4$, partially fluorinated or completely fluorinated counterparts of all such alkyl groups are appropriate, the degree of fluorination being chosen at will from monofluorination up to perfluorination Suitable cycloalkyl and alkylcycloalkyl groups both have typically from 3 to 9 carbon atoms. The cycloalkyl portions can include cyclopropyl, cyclobutyl, cyclopentyl, cyclohexyl, cycloheptyl, cyclooctyl, and cyclononyl, and suitable alkyl portions include those mentioned above. In all cases, both straight-chain and branched embodiments of all such groups are included.

Steroidal antiestrogens which are substantially devoid of estrogenic residual effect (pure antiestrogens) are disclosed in EP-A-0,138,504. Among the large number of compounds described therein, 11-(3,17β-dihydroxy-1,3,5(10)-estratrien-7α-yl)undecanoic acid (N-butyl-N-methyl)amide deserves special emphasis.

J. Bowler et al., in "Steroids" 89:71, describe the particularly high oral efficacy of corresponding steroidal antiestrogens carrying a 2,3,4-heptafluorobutyl group on the amide nitrogen atom.

An increase in estrogenic activity over estradiol upon peroral administration by introduction of a 14α,17α-etheno- or -ethano bridge has been observed in the 14,17α-etheno- and -ethanoestratrienes carrying two hydrogen atoms as substituents on the C-7 atom described in International Patent Application WO 88/01275.

It has now been found that the compounds of this invention according to general Formula I are, upon peroral administration, pure antiestrogens having a stronger antiestrogenic activity than the compounds described in EP-A-0,138,504.

In order to determine the antiestrogenic effect of the compounds according to the invention, inhibition of estradiol-induced uterus and vaginal growth was determined on adult, ovariectomized rats upon peroral administration of the representative compound 11-(3,17-dihydroxy-14α,17α-ethano-1,3,5(10)-estratrien-7α-yl)undecanoic acid (N-butyl-N-methyl)amide (A). The comparison compound utilized was 11-(3,17β-dihydroxy-1,3,5(10)-estratrien-7α-yl)undecanoic acid (N-butyl-N-methyl)amide (B).

Determination of antiestrogenic efficacy upon peroral administration

Sexually mature, female rats (weight approximately 200 g, 6 animals/dose) are ovariectomized 14 days prior to beginning of treatment. The compounds, dissolved in benzyl benzoate/castor oil (1+9), are administered perorally on 5 consecutive days. At the same time, the animals receive 0.3 μg of estradiol in the same vehicle subcutaneously. On the day after the last administration, the animals are sacrificed, uteri and vaginas are excised, and the moist weight is determined. The organ weights are based on 100 g of body weight. The average values and standard deviations are calculated. In order to determine the antiestrogenic efficacy, the percentage inhibition of organ growth was calculated, based on the estradiol-treated standard.

A causes a dose-dependent and pronounced inhibition of the growth of uterus and vagina. With a dose of 30 mg/kg, an almost complete inhibition to the level of the ovariectomized control is achieved.

The antiestrogenic effect of A, in this peroral administration, is superior to the effect of compound B, to be considered as the standard, with regard to maximum inhibitory effect as well as with respect to the dose. These differences can be confirmed statistically ($p<0.05$) in the case of the uterus weight in a dose of 3 and 30 mg/kg, in case of the vagina weight in the 30 mg/kg dose.

Figure 1:
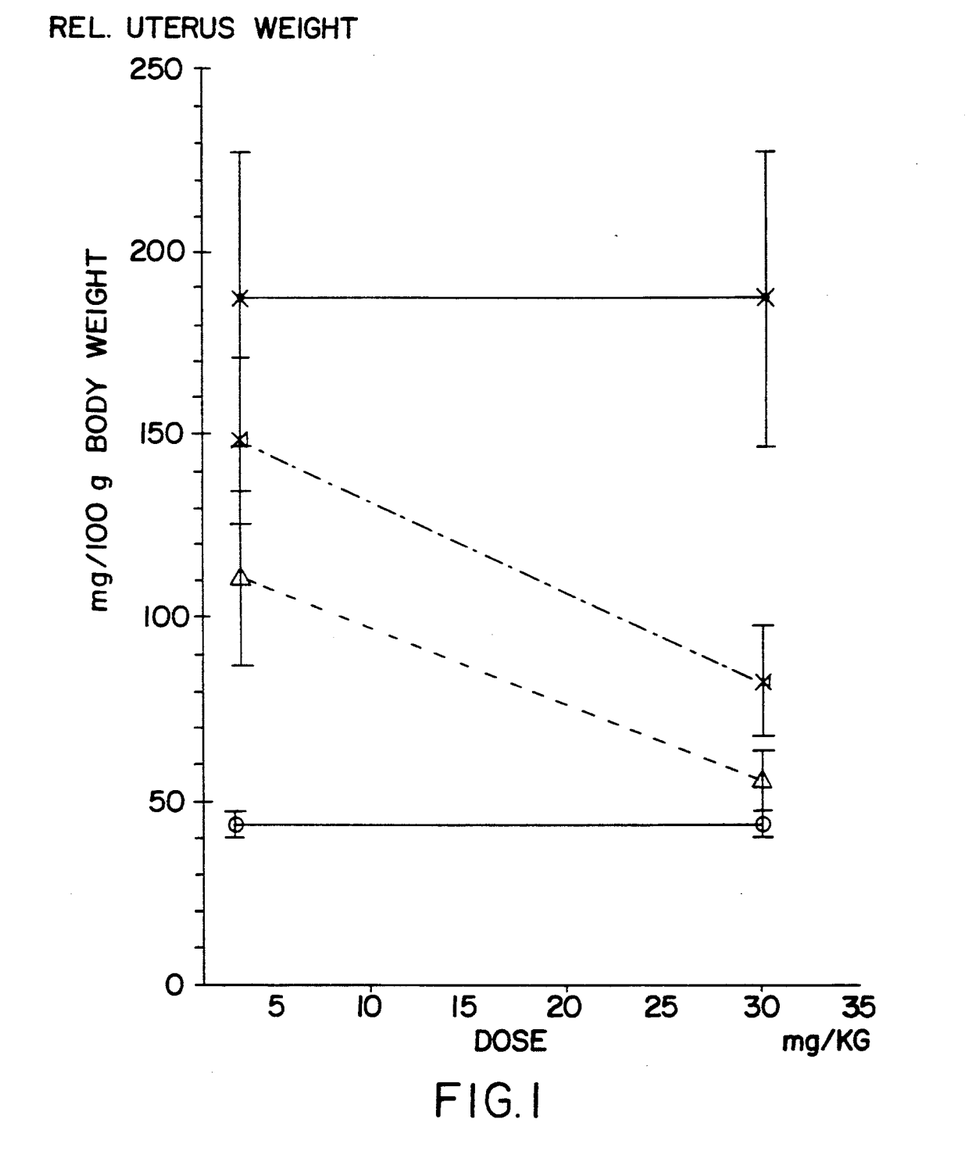
FIG. 1 compares the effect of the compound (A) in accordance with the invention with compound (B), the standard, and with a control and estradiol, in terms of inhibition of uterine growth in ovariectomized, sexually mature rats.
Figure 2:
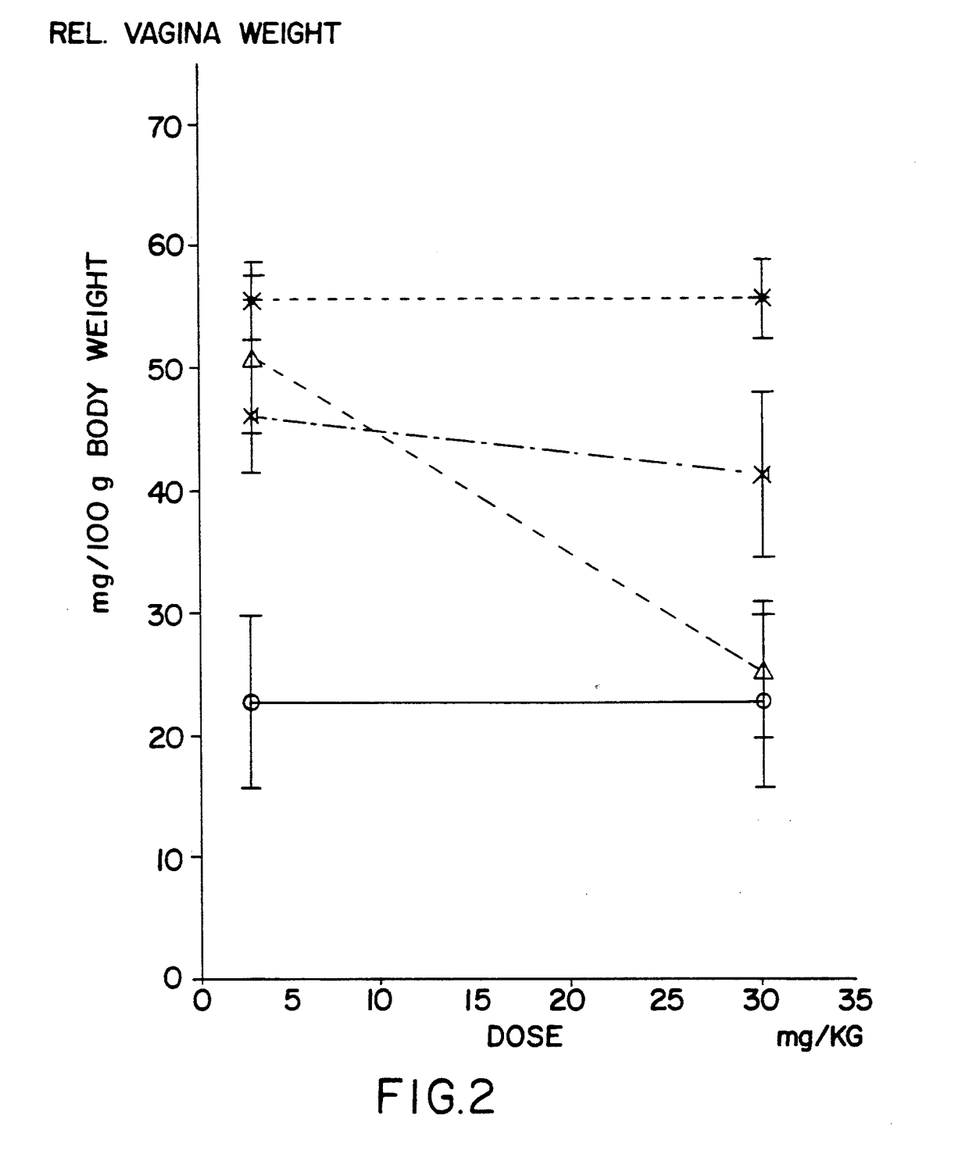
FIG. 2 reports similar data as FIG. 1, in terms of inhibition of vaginal growth.

These results are compiled in Table 1 and illustrated in a mutual comparison for the uterus weights in FIG. 1 and for the vagina weights in FIG. 2.

An estrogenic residual effect of A upon subcutaneous administration cannot be detected either in infantile mice or in infantile rats, as can be seen from the test described below; this test furthermore demonstrates that compound A according to this invention is a strongly active antiestrogen in infantile rats also when administered subcutaneously.

Determination of estrogenic/antiestrogenic activity in infantile mice/rats

Female, infantile mice (21 days old, weight 13-15 g, 6 animals/dose) receive the test compound subcutaneously, dissolved in benzyl benzoate/castor oil (1+9) on 3 (mice) and, respectively, 5 (rats) successive days either solely (estrogen test) or together with estradiol (0.1 μg/mouse; 0.3 μg/rat) the day after the last administration, uteri and vaginas are excised, and the moist weight is determined.

The organ weights are based on 10 g (mouse) and, respectively, 100 g (rat). The average values and standard deviations are calculated. For determining antiestrogenic efficacy, the percentage inhibition of organ growth is calculated, based on the estradiol-treated standard.

Figure 3:
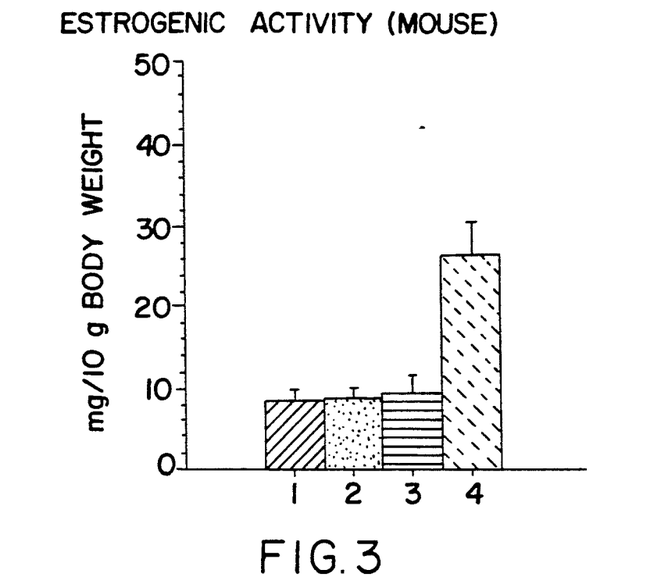
FIGS. 3 and 4 report inhibition data gathered on infantile mice for the same four compounds, in terms of inhibition of vaginal and uterine growth, respectively.
Figure 4:
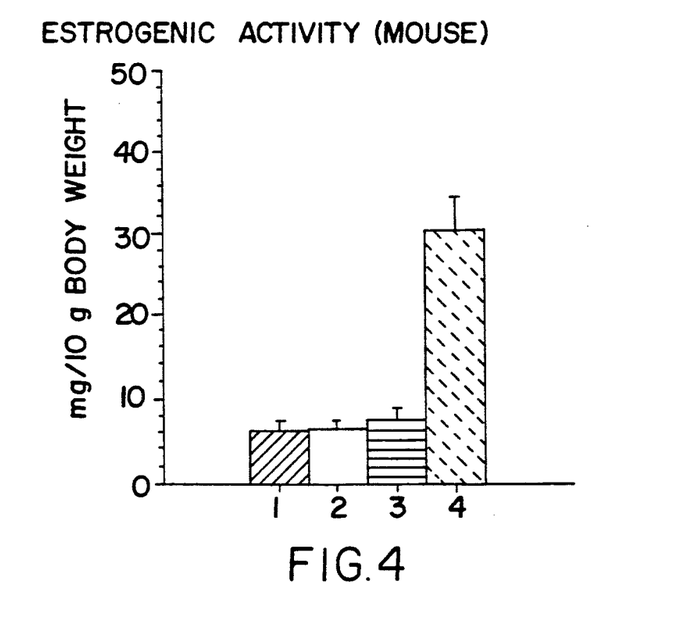

The results with infantile rats are listed in Table 2; FIG. 3 shows that, in infantile mice, compound A and comparison compound B, with a subcutaneous dose of 30 mg/kg, do not show any significant estrogenic effect on the vagina and on the uterus (FIG. 4).

The compounds of this invention are thus suited for the therapy of estrogen-dependent diseases, i.e., those diseases in which the presence of estrogen or excess estrogen causes or aggravates the condition to be treated, for example anovulatory infertility, hyperplasia of the prostate, mamma carcinoma, endometrial carcinoma, and melanoma.

The daily dosage for the treatment of the aforementioned diseases is typically 0.1-25 mg/kg; preferably 1-20 mg/kg, in human patients, this corresponds to a daily dosage of 5-1,250 mg. One dosage unit contains, according to this invention, 5-500 mg of one or several compounds of general Formula I.

Compounds of this invention can be used, e.g., for treatment of mamma carcinoma analogously to the use of the known agent Tamoxifen. Compounds of this invention can be used, e.g., for treatment of hyperplasia of the prostate analogously to the use of the known agent Testolactone. Treatment is in accordance with methods disclosed in the literature, e.g., Steroids, 50, 1987, p. 191-200 and Cancer. Res. (Suppl.) 42, 3387.

The compounds according to this invention are suitable for the production of pharmaceutical compositions and preparations. The pharmaceutical compositions and/or medicinal agents contain, as the active material, one or several of the compounds according to this invention, optionally in a mixture with other pharmacologically and, respectively, pharmaceutically effective substances. The medicinal agents are prepared in the conventional way; the known and customary pharmaceutical auxiliary agents as well as other conventional vehicles and diluents can be employed.

Such vehicles and auxiliary materials are, for example, those recommended and/or listed in the following literature references as auxiliary ingredients for pharmacy, cosmetics, and adjoining fields of art: Ullmans Encyclopädie der technischen Chemie, vol. 4 (1953) pages 1-39; Journal of Pharmaceutical Sciences, vol. 52 (1963), pages 918 et seq., H. v. Czetsch-Lindenwald, "Hilfsstoffe fuer Pharmazie und angrenzende Gebiete" [Auxiliary Agents for Pharmacy and Related Areas]; Pharm. Ind., issue 2, 1961, pages 72 et seq.; Dr. H. P. Fiedler, "lexikon der Hilfsstoff fuer Pharmazie, Kosmetik und angrenzende Gebiete" [Auxiliary Substances Dictionary for Pharmacy, Cosmetics and Related Fields], Cantor KG, Aulendorf in Wuerttemberg, 1971.

The compounds can be administered orally or parenterally, for example intraperitoneally, intramuscularly, subcutaneously or percutaneously. The compounds can also be implanted into the tissue. The quantity of compound to be administered fluctuates within a wide range and can cover any effective amount. In dependence on the condition to be treated and on the type of administration, the quantity of the administered compound can be 0.01-100 mg/kg body weight, preferably 0.1-25 mg/kg of body weight per day, more preferably 1-20 mg/kg/day.

Capsules, pills, tablets, dragees, etc. are suitable for oral administration. The dosage units can contain, beside the active ingredient, a pharmaceutically acceptable vehicle, e.g., amylose, sugar, sorbitol, gelatin, lubricants, silicic acid, talc, etc.

For parenteral administration, the active compounds can be dissolved or suspended in a physiologically compatible diluent. Very frequently, diluents employed are oils with or without addition of a solubilizer, of a surfactant, of a suspension aid or of an emulsifier. Examples for oils utilized herein are olive oil, peanut oil, cottonseed oil, soybean oil, castor oil, and sesame oil.

The compounds can also be used in the form of a depot injection or an implant preparation which can be formulated so that sustained release of active compound is made possible.

Implants can contain, as inert materials, for example biodegradable polymers or synthetic silicones, e.g., silicone rubber. The active agents can furthermore be incorporated into a plaster, for example, for percutaneous administration.

TABLE 1

ANTIESTROGENIC EFFECT ON ADULT, OVARIECTOMIZED RATS

| Compound Dose/Day | Uterus Weight (mg/100 g) | % Inhibition | Vagina Weight (mg/100 g) | % Inhibition |
|---|---|---|---|---|
| Control | 44 ± 3 | — | 23 ± 7 | — |
| Estradiol (E2) 0.3 μg/Animal | 187 ± 41 | — | 55 ± 3 | — |
| Compound A 3 mg/kg | 111 ± 24* | 53 | 51 ± 6 | 13 |
| Compound A 30 mg/kg | 56 ± 8* | 92 | 25 ± 6* | 92 |
| Compound B 3 mg/kg | 148 ± 23 | 27 | 46 ± 5* | 29 |
| Compound B 30 mg/kg | 83 ± 15* | 73 | 41 ± 6* | 44 |

* = significant ($p < 0.05$)

TABLE 2

EFFECT OF COMPOUNDS A AND B ON THE ESTRADIOL-STIMULATED GROWTH OF UTERUS AND VAGINA IN INFANTILE RATS

| Compound Dose/Day | Uterus Weight (mg/100 g) | % Inhibition | Vagina Weight (mg/100 g) | % Inhibition |
|---|---|---|---|---|
| Control | 68.0 ± 15.3* | | 37.5 ± 4.9* | |
| Estradiol (E2) 0.3 μg/Animal Antiestrogen Test | 248.6 ± 35.9 | | 82.4 ± 9.6 | |
| Compound A 30 mg/kg + E2 Estrogen Test | 109.6 ± 10.9* | 77 | 47.9 ± 7.6* | 77 |
| Compound A 30 mg/kg | 49.7 ± 11.1* | | 27.5 ± 5.9* | |

* = significant ($p < 0.05$)

The compounds of general Formula I are prepared according to this invention in that, in the compound of general Formula II the double bond of the 14α,17α-etheno bridge is optionally hydrogenated, the 3-hydroxy function is blocked, the 11-hydroxy group of the 7α-undecyl side chain is oxidized to the carboxylic acid, the corresponding carboxylic acid amide is produced from the carboxylic acid with the amine $H-NR^3R^4$ wherein $R^3$ and $R^4$ have the meanings given in Formula I in the definition of the grouping $R^2$, the blocking group in the 3-position is optionally split off, and subsequently, if desired, the 3-hydroxy group is either partially acetylated or methylated and/or optionally the keto group of the carboxylic acid amide is completely reduced.

By the use of an amine correspondingly fluorinated in the alkyl chains $R^3$ and/or $R^4$ in process step (p) of the following examples, it is possible to prepare, analogously to the described step (p), the side-chain-fluorinated compounds according to this invention. The side-chain-fluorinated amines are commercially available or are accessible to methods with which a person skilled in the art is familiar.

The partial acylation or alkylation of the 3-hydroxy group takes place according to conventional methods. A blockage of the 17-hydroxy group may be necessary in certain cases.

The complete reduction of the keto group of the carboxylic acid amide can take place with lithium aluminum hydride or similar reducing agents in accordance with likewise conventional processes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 25 507.7, filed Jul. 28, 1989, are hereby incorporated by reference.

EXAMPLES

Example 1

11-(14α,17α-Ethano-3,17-dihydroxy-1,3,5(10)-estratrien-7α-yl)undecanoic Acid (N-n-Butyl-N-methyl)amide (a) 11-Bromoundecyl-tert-butyldimethylsilyl Ether 175 g of 11-bromoundecanol (Fluka) is dissolved in 420 ml of tetrahydrofuran and combined at 25° with 101 g of imidazole as well as 130.1 g of tert-butyldimethylsilyl chloride in 140 ml of tetrahydrofuran, and agitated for 2 hours at 25°. For the working up step, 1.2 l of diethyl ether is added, the thus-precipitated hydrochloride is filtered off, the mixture concentrated to dryness under vacuum and chromatographed on silica gel with hexane/ethyl acetate, yielding 509.6 g of 11-bromoundecyl-tert-butyldimethylsilyl ether as an oil.

(b) 7-[11-(Dimethyl-tert-butylsilyloxy)undecyl]-4-estrene-3,17-dione 7.4 g of magnesium filings is placed into 31 ml of tetrahydrofuran and combined within 1.5 hours with a solution of 113 g of 11-bromoundecyl-tert-butyldimethylsilyl ether in 310 ml of tetrahydrofuran. After one hour at a bath temperature of 100°, the mixture is diluted with 157 ml of tetrahydrofuran, cooled to −30°, mixed with 29.5 g of copper(I) iodide, stirred for 0.2 hour at −30°, a solution of 25 g of 4,6-estradiene-3,17-dione [Kalvoda, J., and Anner, G., Helv. Chim. Acta 50 : 269 (1967)]in 220 ml of tetrahdyrofuran is added dropwise, and the mixture is further stirred for 1.5 hours at −30°. Then, 18.7 ml of glacial acetic acid is added, the mixture is concentrated under vacuum, poured on water, suctioned off through "Celite", rinsed with ethyl acetate, extracted twice with ethyl acetate, washed with water and sodium chloride solution, dried over sodium sulfate, concentrated to dryness under vacuum, and chromatographed on silica gel with hexane/ethyl acetate, thus obtaining 88.6 g of 7α-[11-(dimethyl-tert-butyl-silyloxy)undecyl]-4-estrene-3,17-dione, $[\alpha]_D = 54.4°$, as an oil, as well as 55.2 g of 7β-[11-(dimethyl-tert-butylsilyloxy)undecyl]-4-estrene-3,17-dione, mp 65°.

(c) 7α-(11-Acetoxyundecyl)-4-estrene-3,17-dione 28.3 g of 7α-[11-(dimethyl-tert-butylsilyloxy)-undecyl]-4-estrene-3,17-dione is stirred in 141 ml of tetrahydrofuran with 156 ml of glacial acetic acid and 78 ml of water for 2 hours at 50°. Then the mixture is concentrated to dryness under vacuum. The crude 7α-(11-hydroxyundecyl)-4-estrene-3,17-dione obtained in this way is agitated with 140 ml of pyridine and 70 ml of acetic anhydride for 15 hours at 25°. For working up the mixture, the latter is cooled to 0°, combined diluted with diethyl ether, washed with sodium bicarbonate and sodium chloride solution, dried over sodium sulfate, concentrated to dryness under vacuum, and chromatographed on silica gel with dichloromethane/ethyl acetate, yielding 22.4 g of 7α-(11-acetoxyundecyl)-4-estrene-3,17-dione, [α]$_D$=62.4°, as an oil.

(d)
3-Acetoxy-7α-(11-acetoxyundecyl)estra-1,3,5(10)-trien-17-one 10.5 g of 7α-(11-acetoxyundecyl)-4-estrene-3,17-dione in 58.5 ml of acetonitrile is added to a solution of 9.1 g of copper(II) bromide and 1.78 g of lithium bromide in 141 ml of acetonitrile and heated under reflux for 0.5 hour. Then the mixture is cooled to 0°, gradually combined with 235 ml of sodium bicarbonate solution, extracted three times with ethyl acetate, washed with water and sodium chloride solution, dried over sodium sulfate, concentrated to dryness under vacuum, and chromatographed on silica gel with hexane/ethyl acetate, thus obtaining 7.5 g of 3-acetoxy-7α-(11-acetoxyundecyl)-1,3,5(10)-estratrien-17-one, [α]$_D$=75.8°, as an oil.

(e)
3-Acetoxy-7α-(11-acetoxyundecyl)-17,17-ethylenedioxy-1,3,5(10)-estratriene 7.85 g of 3-acetoxy-7α-(11-acetoxyundecyl)-1,3,5(10)-estratrien-17-one is stirred under reflux in 51 ml of dichloromethane and 51 ml of ethylene glycol with 24 ml of trimethyl orthoformate and 159 mg of p-toluenesulfonic acid for 0.5 hour. For working up purposes, the mixture is diluted with dichloromethane, washed with sodium bicarbonate and sodium chloride solutions, dried over sodium sulfate, concentrated to dryness under vacuum, and chromatographed on silica gel with hexane/ethyl acetate, yielding 6.5 g of pure 3-acetoxy-7α-(11-acetoxyundecyl)-17,17-ethylenedioxy-1,3,5(10)-estratriene, [α]$_D$=13.4°, as an oil.

(f)
3-Acetoxy-7o-(11-acetoxyundecyl)-16α-bromo-17,17-ethylenedioxy-1,3,5(10)-estratriene 6.4 g of 3-acetoxy-7o-(11-acetoxyundecyl)-17,17-ethylenedioxy-1,3,5(10)-estratriene is combined, in 116 ml of tetrahydrofuran, at 0° with 9.31 g of pyridine hydrobromide perbromide in portions. Then the mixture is diluted with ethyl acetate, washed with sodium sulfite solution, water, and sodium chloride solution, dried over sodium sulfate, concentrated to dryness under vacuum, and chromatographed on silica gel with hexane/ethyl acetate, thus obtaining 5.32 g of pure 3-acetoxy-7α-(11-acetoxyundecyl)-16-bromo-17,17-ethylenedioxy-1,3,5(10)-estratriene, [α]$_D$=18.8°, as an oil.

(g)
7α-(11-Hydroxyundecyl)-17,17-ethylenedioxy-1,3,5(10),15-estratetraen-3-ol 5.32 g of 3-acetoxy-7α-(11-acetoxyundecyl)-16β-bromo-17,17-ethylenedioxy-1,3,5(10)-estratriene is stirred in 80 ml of diemthyl sulfoxide and 8 ml of methanol with 8 g of potassium hydroxide for 6.5 hours at a bath temperature of 90°. Then the mixture is precipitated with ice/aqueous sodium chloride solution, taken up in dichloromethane, washed until neutral, dried over sodium sulfate, concentrated to dryness under vacuum, and chromatographed on silica gel with hexane/ethyl acetate, thus producing 2.74 g of pure 7α-(11-hydroxyundecyl)-17,17-ethylenedioxy-1,3,5(10)-estratetraen-3-ol.

(H)
7α-(11-Hydroxyundecyl)-1,3,5(10),15-estratetraen-3-ol-17-one 2.6 g of 7α-(11-hydroxyundecyl)-17,17-ethylenedioxy-1,3,5(10),15-estratetraen-3-ol is stirred in 57 ml of acetone and 6.6 ml of water at 25° with 164 mg of p-toluenesulfonic acid for 2.5 hours. Then the mixture is concentrated to one-third, precipitated with ice/aqueous sodium chloride solution, filtered off, taken up in dichloromethane, washed neutral, dried over sodium sulfate, and concentrated to dryness under vacuum, thus obtaining 2.3 g of crude 7α-(11-hydroxyundecyl)-1,3,5(10),15-estratetraen-3-ol-17-one, [α]$_D$=−14.0°, as an oil.

(j)
3,17-Diacetoxy-7α-(11-acetoxyundecyl)-1,3,5(10),14,16-estrapentaene 2.2 g of 7α-(11-hydroxyundecyl)-1,3,5(10),15-estratetraen-3-ol-17-one is stirred in 37 ml of acetic anhydride with 513 mg of p-toluenesulfonic acid for 3 hours at 25°. For working up purposes, the mixture is precipitated with pyridine/sodium chloride solution, taken up in ethyl acetate, washed with sodium bicarbonate and sodium chloride solutions, dried over sodium sulfate, concentrated to dryness under vacuum, and chromatographed on silica gel with hexane/ethyl acetate; yield: 2.0 g of 3,17-diacetoxy-7α-(11-acetoxyundecyl)-1,3,5(10),14,16-estrapentaene, [α]$_D$=128.6°, as an oil.

(k)
3,17-Diacetoxy-7α-(11-acetoxyundecyl)-14α,17α-etheno-16β-phenylsulfonyl-1,3,5(10)-estratriene 1.9 g of 3,17-diacetoxy-7α-(11-acetoxyundecyl)-1,3,5(10),14,16-estrapentaene is stirred in a pressurized vessel in 20 ml of benzene with 1.69 g of phenylvinylsulfone for 120 hours at a bath temperature of 170°. Then the mixture is flushed with ethyl acetate into a glass flask, concentrated under vacuum, and chromatographed on silica gel with hexane/ethyl acetate, thus obtaining 1.61 g of 3,17-diacetoxy-7α-(11-acetoxyundecyl)-14α,17α-etheno-16β-phenylsulfonyl-1,3,5(10)-estratriene, [α]$_D$=76.6°, as a foam.

(l)
14α,17α-Etheno-7α-(11-hydroxyundecyl)-1,3,5(10)-estratriene-3,17-diol 1.3 g of 3,17-diacetoxy-7α-(11-acetoxyundecyl)-14α,17α-etheno-16β-phenylsulfonyl-1,3,5(10)-estratriene in tetrahydrofuran is added dropwise at −78° into 50 ml of liquid ammonia, combined in portions with 290 mg of lithium, and stirred for 2 hours at −70°. Then the mixture is combined with 15 ml of ammonium chloride solution at −50°, the ammonia is removed by evaporation, the mixture is diluted with ethyl acetate, washed with water and sodium chloride solution, dried over sodium sulfate, concentrated to dryness under vacuum, and chromatographed on silica gel with hexane/ethyl acetate, thus producing 0.452 g of 14α,17α-etheno-7α-(11-hydroxyundecyl)-1,3,5(10)-estratriene-3,17-diol, [α]$_D$=86.3°, as an oil.

(m)
14α,17α-Ethano-7α-(11-hydroxyundecyl)-1,3,5(10)-estratriene-3,17-diol 530 mg of 14α,17α-etheno-7α-(11-hydroxyundecyl)-1,3,5(10)-estratriene-3,17-diol is dissolved in 10 ml of ethyl acetate and hydrogenated with 100 mg of palladium 10% on carbon for 2.5 hours at 25° and under 1 bar. For working up purposes, the mixture is suctioned off via "Celite", rinsed with ethyl acetate, dried over sodium sulfate, concentrated to dryness under vacuum, and chromatographed on silica gel with hexane/ethyl acetate, thus producing 400 mg of pure 14α,17α-ethano-7α-(11-hydroxyundecyl)-1,3,5(10)-estratriene-3,17-diol as a foam.

(n)
3-Benzoyloxy-14α,17α-ethano-7α(11-hydroxyundecyl)-1,3,5(10)-estratrien-17-ol 1.0 g of 14α,17α-ethanol-7α-(11-hydroxyundecyl)-1,3,5(10)-estratriene-3,17-diol is combined in 11.3 ml of acetone at 0° with 3.2 ml of 0.1N sodium hydroxide solution and 0.3 ml of benzoyl chloride and further stirred for 0.5 hour at 0°. For working up purposes, the mixture is poured on sodium bicarbonate, extracted three times with ethyl acetate, washed with sodium chloride solution, dried over sodium sulfate, concentrated to dryness under vacuum, and chromatographed on silica gel with hexane/ethyl acetate, thus obtaining 1.0 g of 3-benzoyloxy-14α,17α-ethano-7α(11-hydroxyundecyl)-1,3,5(10)-estratrien-17-ol, $[\alpha]_D=42.1°$, as a foam.

(o)
11-(3-Benzoyloxy-14α,17α-ethano-17-hydroxy-1,3,5(10)-estratrien-7α-yl)undecanoic Acid 1.0 g of 3-benzoyloxy-14α,17α-ethanol-7α-(11-hydroxyundecyl)-1,3,5(10)-estratrien-17-ol is combined in 17 ml of acetone gradually with 1.0 ml of Jones reagent at 0° and stirred for 0.5 hour. For working up purposes, 1.3 ml of 2-propanol is added, the mixture is concentrated to dryness under vacuum, 0.1N hydrochloric acid is added, the mixture is extracted four times with dichloromethane, washed with sodium chloride solution, dried over sodium sulfate, concentrated to dryness under vacuum, and chromatographed on silica gel with dichloromethane/acetone, yielding 860 mg of 11-(3-benzoyloxy-14α,17α-ethanol-17-hydroxy-1,3,5(10)-estratrien-7α-yl)undecanoic acid, $[\alpha]_D=39.8°$, as a foam.

(p)
11-(3-Benzoyloxy-14α,17α-ethanol-17-hydroxy-1,3,5(10)-estratrien-7α-yl)undecanoic Acid (N-n-Butyl-N-methyl)amide 810 mg of 11-(3-benzyloxy-14α,17α-ethano-17-hydroxy-1,3,5(10)-estratrien-7α-yl)undecanoic acid is stirred in 14 ml of dichloromethane at −10° with 0.21 ml of N-methylmorpholine and 0.24 ml of chloroformic acid isobutyl ester for 0.5 hour. Subsequently, 0.27 ml of N-methylbutylamine is gradually added dropwise, and the mixture is stirred for 1 hour at 25°. For working up purposes, the mixture is combined with sodium bicarbonate solution, diluted with dichloromethane, washed with water and sodium chloride solution, dried over sodium sulfate, concentrated to dryness under vacuum, and chromatographed on silica gel with hexane/ethyl acetate, yielding 631 mg of 11-(3-benzoyloxy-14α,17α-ethano-17-hydroxy-1,3,5(10)-estratrien-7α-yl)undecanoic acid (N-n-butyl-N-methyl)amide.

(q)
11-(14α,17α-Ethano-3,17-dihydroxy-1,3,5(10)-estratrien-7α-yl)undecanoic Acid (N-n-Butyl-N-methyl)amide

601 mg of 11-(3-benzoyloxy-14α,17α-ethanol-17-hydroxy-1,3,5(10)-estratrien-7α-yl)undecanoic acid (N-n-butyl-N-methyl)amide is stirred in 10 ml of methanol and 5 ml of tetrahydrofuran with 5 ml of 1N sodium hydroxide solution for 0.5 hour at 25°. The mixture is then neutralized with 1N hydrochloric acid, concentrated under vacuum, poured on water, extracted four times with dichloromethane, washed with sodium chloride solution, dried over sodium sulfate, concentrated to dryness under vacuum, and chromatographed on silica gel with dichloromethane/acetone, thus obtaining 593 mg of 11-(14α,17α-ethanol-3,17-dihydroxy-1,3,5(10)-estratrien-7α-yl)undecanoic acid (N-n-butyl-N-methyl)amide, $[\alpha]_D=22.7°$, as a foam.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 14,17α-Etheno- or -ethanoestratriene of Formula I wherein
X is a —CH₂—CH₂ or bridge, R¹ is hydrogen, a C₁₋₁₅-acyl, benzoyl, C₁₋₁₅-alkyl, C₃₋₉-cycloalkyl or C₃₋₅-alkylcycloalkyl, and
R² is and R³ and R⁴ each independently are hydrogen, C₁₋₈-alkyl, or fluorinated C₁₋₈-alkyl.

2. A 14,17α-Etheno- or -ethanoestratriene according to claim 1, wherein $R^1$ is hydrogen, $C_{1-6}$-acyl, benzoyl, $C_{1-6}$-alkyl or $C_{3-6}$-cycloalkyl.

3. A 14,17α-Etheno- or -ethanoestratriene according to claim 1, wherein $R^1$ is hydrogen, acetyl or methyl.

4. A 14,17α-Etheno- or -ethanoestratriene according to claim 1, wherein $R^3$ is $C_{1-8}$-alkyl and $R^4$ is a partially or completely fluorinated $C_{1-8}$-alkyl group.

5. A 14,17α-Etheno- or -ethanostratriene according to claim 4, wherein $R^3$ is methyl and $R^4$ is 2,3,4-heptafluorobutyl.

6. 11-(14α,17α-Ethano-3,17-dihydroxy-1,3,5(10)-estratrien-7α-yl)undecanoic acid (N-n-butyl-N-methyl)amide, or 11-(14α,17α-ethano-3,17-dihydroxy-1,3,5(10)-estratrien-7α-yl)undecanoic acid (N-2,3,4-heptafluoro-n-butyl-N-methyl)amide, each a compound of claim 1.

7. A pharmaceutical composition, comprising a compound of claim 1 and a pharmaceutically acceptable carrier.

8. A method for the treatment of an estrogen-dependent disease, comprising administering to a host in need of such treatment an amount of a compound of claim 1 effective to reduce estrogen levels in said host.

9. A method for the treatment of an anovulatory infertility, comprising administering to a host in need of such treatment an amount of a compound of claim 1 effective to reduce estrogen levels in said host.

10. A method for the treatment of mamma carcinoma, endometrial carcinoma or a melanoma, comprising administering to a host in need of such treatment an amount of a compound of claim 1 effective to reduce estrogen levels in said host.

11. A compound of Formula II